United States Patent
Kosierkiewicz

(10) Patent No.: US 9,962,096 B1
(45) Date of Patent: May 8, 2018

(54) SYSTEM AND METHOD TO ANALYZE WAVEFORMS FOR ELECTROMYOGRAPHY TESTING

(71) Applicant: Tomasz Andrzej Kosierkiewicz, Mount Vernon, IL (US)

(72) Inventor: Tomasz Andrzej Kosierkiewicz, Mount Vernon, IL (US)

( * ) Notice: Subject to any disclaimer, the term of this patent is extended or adjusted under 35 U.S.C. 154(b) by 82 days.

(21) Appl. No.: 14/604,715

(22) Filed: Jan. 24, 2015

Related U.S. Application Data

(60) Provisional application No. 61/931,591, filed on Jan. 25, 2014.

(51) Int. Cl.
| | |
|---|---|
| *A61B 5/04* | (2006.01) |
| *A61B 5/0488* | (2006.01) |
| *H04R 29/00* | (2006.01) |
| *A61B 7/00* | (2006.01) |
| *A61B 5/00* | (2006.01) |

(52) U.S. Cl.
CPC ........ *A61B 5/04012* (2013.01); *A61B 5/0488* (2013.01); *H04R 29/008* (2013.01); *A61B 5/4519* (2013.01); *A61B 7/006* (2013.01)

(58) Field of Classification Search
CPC . A61B 5/04012; A61B 5/0488; A61B 5/4519; A61B 7/006; H04R 29/008
USPC .................................................. 600/546, 586
See application file for complete search history.

(56) References Cited

U.S. PATENT DOCUMENTS

| | | | | |
|---|---|---|---|---|
| 5,092,343 | A * | 3/1992 | Spitzer ................. | A61B 5/0488 128/925 |
| 2004/0254617 | A1* | 12/2004 | Hemmerling .......... | A61B 7/006 607/48 |
| 2013/0268240 | A1* | 10/2013 | Thorn ................... | G01D 21/00 702/180 |

* cited by examiner

*Primary Examiner* — Devin Henson
(74) *Attorney, Agent, or Firm* — Loza & Loza, LLP; Jessica Smith

(57) ABSTRACT

A device includes an EMG processing application operable with a processing module to receive audio output from EMG testing, wherein the audio output represents electrical activity of at least one muscle. The EMG processing application is operable to process the audio output to detect at least one type of waveform of a plurality of types of waveforms from the audio output and display the detected at least one type of waveform.

12 Claims, 6 Drawing Sheets

SYSTEM AND METHOD TO ANALYZE WAVEFORMS FOR ELECTROMYOGRAPHY TESTING

CROSS-REFERENCE TO RELATED PATENTS

The present U.S. Utility Patent Application claims priority pursuant to 35 U.S.C. § 119(e) to U.S. Provisional Application Ser. No. 61/931,591, entitled, "SYSTEM AND METHOD TO ANALYZE WAVEFORMS FOR ELECTROMYOGRAPHY TESTING," filed Jan. 25, 2014, which is incorporated by reference herein and made part of the present U.S. Utility Patent Application for all purposes.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not applicable.

BACKGROUND

Technical Field

This disclosure relates generally to medical devices and more particularly, but not exclusively, to systems and methods for electromyography testing.

Description of Related Art

The statements in this section provide a description of related art and are not admissions of prior art. An examiner, such as a physician, neurologist, or physiatrist, performs nerve conduction studies on patients. A complementary part of nerve conduction studies is electromyography (EMG). EMG results can reveal nerve dysfunction, muscle dysfunction or problems with nerve-to-muscle signal transmission. EMG testing includes a technique for recording electrical activity produced by skeletal muscles. Motor neurons transmit electrical signals that cause muscles to contract. In one type of EMG testing, a needle electrode is inserted directly into a muscle and records the electrical activity in that muscle. Electrical activity of the muscle is sensed by the electrode. An EMG translates these signals into graphs of waveforms displayed on a monitor. In addition, an audio-amplifier is often used to record an audio representation of the electrical activity. The examiner may listen to the audio representation and/or view the waveforms on the monitor to evaluate the electrical activity of the muscle as normal or abnormal. The interpretation of an EMG test is thus very subjective due to the evaluation of the waveforms by the Examiner.

As such, a need exists to improve EMG testing and in particular to provide a more objective analysis of the waveforms produced by the EMG testing.

SUMMARY

In an embodiment, a device includes an EMG processing application operable with a processing module to receive audio output of an EMG device, wherein the audio output represents electrical activity of at least one muscle; process the audio output to detect at least one type of waveform of a plurality of types of waveforms from the audio output; and display the detected at least one type of waveform.

BRIEF DESCRIPTION OF THE SEVERAL VIEWS OF THE DRAWINGS

Some embodiments of apparatus and/or methods in accordance with embodiments of the disclosure are now described, by way of example only, and with reference to the accompanying drawings, in which.

DETAILED DESCRIPTION

The description and drawings merely illustrate the principles of various embodiments. It will thus be appreciated that those skilled in the art will be able to devise various arrangements that, although not explicitly described or shown herein, embody the principles herein and in the claims and fall within the spirit and scope of the disclosure. Furthermore, all examples recited herein are principally intended expressly to be only for pedagogical purposes to aid the reader in understanding the principles of the embodiments and the concepts contributed by the inventor to furthering the art, and are to be construed as being without limitation to such specifically recited examples and conditions. Moreover, all statements herein reciting principles, aspects, and embodiments, as well as specific examples thereof, are intended to encompass equivalents thereof.

Figure 1:
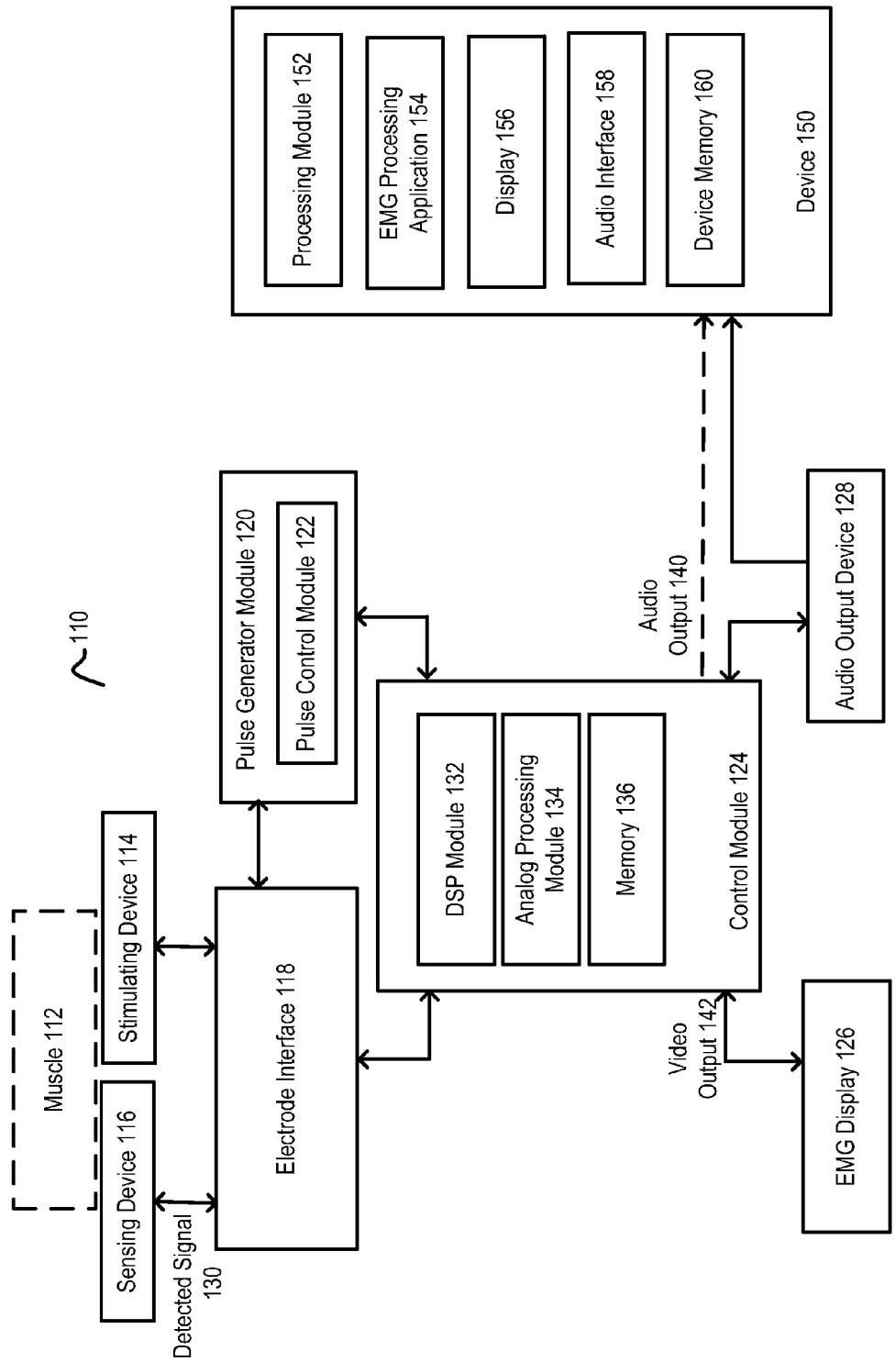
FIG. 1 illustrates a schematic block diagram of an embodiment of a system for performing EMG testing.

FIG. 1 illustrates a schematic block diagram of an embodiment of an EMG system 110 for performing EMG testing. In an embodiment, the EMG system 110 is operable to activate a muscle 112 and record electrical activity responses from the muscle 112. The EMG system 110 detects the electrical potential generated by muscle cells when these cells are electrically or neurologically activated. In an embodiment, the muscle 112 is a human muscle but may also be a non-human muscle such as from an animal. The EMG system 110 includes a stimulating device 114, such as an electrode or needle, for stimulating nerves that activate the muscle 112. The EMG system 100 also includes a sensing device 116, such as another electrode or needle, for recording the electrical activity from the muscle 112 in response to the stimulation of the nerve. Generally, the sensing device 116 includes EMG electrodes placed on the surface of the skin overlying the muscles being evaluated, or needle electrodes which penetrate the tissue being studied.

In addition to these active electrodes, a ground reference electrode is generally also applied to the patient.

An electrode interface 118 is operably coupled to the stimulating device 114 and sensing device 116 and to pulse generator module 120. The pulse generator module 120 includes a pulse control module 122 that communicates with the stimulating device 114, sensing device 116 and to control module 124. The pulse generator module 120 receives commands from the control module 124, such as registration information, transmission frequency commands, amplifier gain commands, transmitter control commands, power saving mode, etc. The pulse generator module 120 processes these commands and responsively configures the stimulating devices 114 and sensing devices 116 accordingly.

In another embodiment, during EMG testing, the muscle 12 may not be stimulated by stimulating device 114. Instead, the sensing device 116 senses electrical activity during normal motion of the muscle 112 or activation neurologically.

The detected signal 130 from the sensing devices 116 is generally weak and typically measured in microvolts. As such, the electrical interface 118 amplifies the detected signal 130 sensed from the muscle 112. Alternatively, the electrical interface 118 transmits the detected signal 130 to the control module 114 that amplifies and processes the detected signal 130. For example, control module 114 includes a digital signal processing (DSP) module 134 and analog processing module 134 that process the detected signal 130. For example, the analog processing module may include a preamplifier followed by one or more additional stages of amplification that boost the detected signal to a usable level as well as filters that minimize the effects of interference arising from sources other than the muscles being studied.

In an embodiment, the DSP module 134 includes an A/D converter that converts the amplified detected signal to a digital signal for further processing. For example, the DSP module may perform rectification of the amplified signal to a single polarity frequency (usually positive). The purpose of rectifying a signal is to ensure the raw signal does not average zero, due to the signal having positive and negative components. The DSP module 132 may analyze the signal and calculate a mean, integration and fast fourier transform (FFT) of the signal. The DSP module 132 and analog processing module 134 may be one module or split into multiple modules with different inputs and outputs.

In an embodiment, the control module 124 further includes a memory 136 to store the received detected signal and processed signals, such as the video output 142 and audio output 140. The audio output 140 is transmitted to audio output device 128, such as a speaker or earphones. The video output 142 is transmitted to an EMG display 126, such as a computer monitor, TV screen or other type of display.

In operation during EMG testing, the pulse control module 122 activates the pulse generator module 120 to transmit an electrical pulse to muscle 112 or associated nerve which activates the muscle 112. The electrical activity in response from the muscle 112 is sensed by the sensing device 116 as detected signal 130. The detected signal 130 is transmitted to the analog processing module 134 and/or DSP module 132 to generate the video output 142 and audio output 140. The audio output 140 is transmitted to the audio output device 128, such as a speaker or earphone, so that the examiner can listen to the audio output 140. In addition the detected signal 130, audio output 140 and/or video output 142 are selectively stored in memory 136 by the control module 124.

A motor unit is defined as one motor neuron and the muscle fibers that it innervates. When a motor unit fires, the impulse (called an action potential) is carried down the motor neuron to the muscle. The area where the nerve contacts the muscle is called the neuromuscular junction, or the motor end plate. After the action potential is transmitted across the neuromuscular junction, an action potential is elicited in all of the innervated muscle fibers of that particular motor unit. The sum of all this electrical activity is known as a motor unit action potential (MUP). This electrophysiologic activity from multiple motor units is the detected signal 130 typically evaluated during EMG testing. The composition of the motor unit, the number of muscle fibers per motor unit, the metabolic type of muscle fibers and many other factors affect the shape of the motor unit potentials (MUPs). EMG signals are essentially made up of superimposed motor unit action potentials (MUPs) from several motor units.

For a thorough analysis, the measured EMG signals can be decomposed into their constituent MUPs. MUPs from different motor units tend to have different characteristic shapes, while MUPs recorded by the same electrode from the same motor unit are typically similar. Notably MUP size and shape depend on where the electrode is located with respect to the fibers and so can appear to be different if the electrode moves position. The electrical source is the muscle membrane potential of about −90 mV. Measured EMG potentials range between less than 50 µV and up to 20 to 30 mV, depending on the muscle under observation.

Typical repetition rate of muscle motor unit firing is about 7-20 Hz, depending on the size of the muscle (eye muscles versus seat (gluteal) muscles), previous axonal damage and other factors. Damage to motor units can be expected at ranges between 450 and 780 mV. A variety of different MUP waveforms are generated in normal and diseased muscles. Currently, an automated machine cannot recognize the various types of MUP waveforms or distinguish a number of MUP waveforms. Clinical EMG testing therefore relies not only on an electromyographer's ability to recognize individual MUP waveforms occurring alone, but also occurring in combination with other MUP waveforms. Currently, an electromyographer must learn to recognize these MUP waveforms empirically by visually recognizing the MUP waveforms on the EMG display 126 or by hearing the audio output 140 representing the waveforms on the audio output device 128.

In an embodiment, a device 150 is operable to receive and process the audio output 140 from the EMG testing and to determine one or more types of MUP waveforms occurring alone or occurring in combination with other MUP waveforms in the audio output 140. The device 150 includes a processing module 52, EMG processing application 154, display 156 and audio interface 158 and device memory 160. The device 150 is a mobile device, such as a laptop, smartphone, smart tablet, etc. In another embodiment, the device 150 or one or more parts of the device 150, such as EMG processing application 154, is incorporated into the EMG system 110, such as part of the control module 124.

In an embodiment, device 150 receives audio output 140 from the EMG system 110. For example, the device 150 includes an audio interface 158 such as a microphone that is operable to detect the audio from the audio output device 128. In another embodiment, the device 150 is operably coupled either wirelessly or wired to the control module 124 or audio output device 128 to receive the audio output 140. The display 156 may be a touch screen to select and control the device 150 or the device 150 may also include other user interfaces such as keyboards, touchpads, etc.

The device 150 is operable to determine a type of waveform from the audio output 140. Different types of waveforms have distinct sound patterns. For example, the device 150 is operable to determine that a waveform is one type of a plurality of types of waveforms from its sound pattern. In an embodiment, the device 150 is also operable to quantify a number of sources of the waveforms in the audio output 140, e.g. a number of motor unit action potential (MUP) waveforms. The device 150 is then operable to record and display the results on display 156. The results are stored within the device memory 160 of the device 150. For example, the results on the display 156 may include a table such as Table 1 below.

When sufficient data is received, the EMG processing application 154 determines one or more types of waveforms and displays the results 208 in a window or tab on the device display 156. The results may also be recorded in the device memory 150 automatically or by selecting a record results 210 option. This process may be repeated for a plurality of muscles in one group of muscles 200 and/or for a plurality of muscles 202 in different groups of muscles 200.

When EMG testing is complete, a list of muscles 202 shows the sampling result 206 for an examined muscle as either green, meaning adequate sampling, or as red, meaning inadequate sampling. Adequate sampling may also be signaled to a specific sound. Selecting a completed muscle 202 displays the electrical activity recording allowing for additional review. Alternatively, a list of time based events for

TABLE 1

Results

| | | Insertional | Spontaneous Activity | | | | Volitional Activity | | | | Recruitment | | |
| --- | --- | --- | --- | --- | --- | --- | --- | --- | --- | --- | --- | --- | --- |
| | | | | | | | MUP | MUP | MUP | MUP | Max | Max | |
| | | Insertional | Fibs | +Wave | Fasics | Poly | Amp | Dur | Config | Pattern | Amp | Pattern | MaxEffort |
| Gastrocnemius Medial Head | R | Normal | None | None | Few | None | Decr | Decr | Poly | Norm | SI Decr | Reduced | Max |
| Tibialis Anterior | R | Increased | None | 1+ | None | None | Norm | Norm | Poly | Norm | SI Decr | Reduced | Max |
| Vastus Lateralis | R | Normal | None | None | None | None | Norm | Norm | Poly | Norm | Norm | Reduced | Max |
| Vastus Medialis | R | Normal | None | None | None | None | Norm | Norm | Norm | Norm | SI Decr | Reduced | Max |

The EMG processing application 154 running on the processing module 152 of the device 150 includes sound pattern recognition software. The EMG processing application 154 is operable to process and correlate the sound pattern associated with particular type of waveform. The type of the waveform is then output and displayed on the display 156 and may be stored within the device memory 150.

Figure 2:
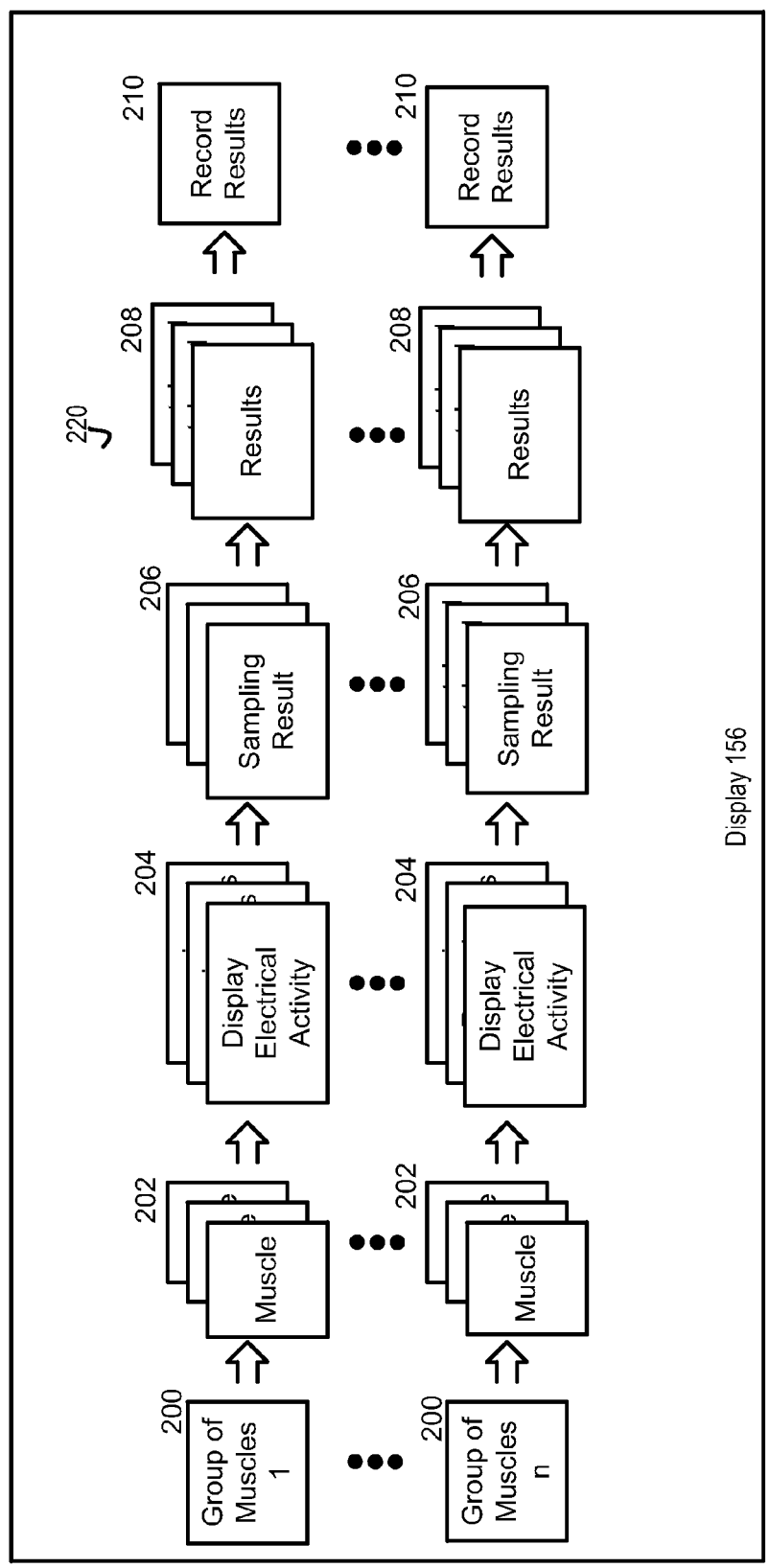
FIG. 2 illustrates a schematic block diagram of an embodiment of a graphical user interface displayed on a device for analyzing EMG testing results.

FIG. 2 illustrates a graphical user interface (GUI) 220 displayed on the display 156 of the device 150. The GUI 220 is only exemplary of the various options and information that may be displayed. The GUI 220 may be separated into a number of different windows or menus or include additional or alternative windows or menus. In an embodiment, the GUI 220 includes an option to select a muscle being tested by the EMG system. The GUI displays a plurality of group of muscles 200 for a patient from a drop down menu or window. The GUI 220 then displays a plurality of muscles 202 for the selected group of muscles. One of the plurality of muscles 202 is then selected. The device 150 then displays the electrical activity received as the audio output 140 and associates it with the selected muscle 202.

For example, during EMG testing of the muscle, the device 150 receives the audio output 140 using a microphone placed in audible distance from the audio output device 128, such as a speaker, of the EMG system 110. A user of the device 150 selects a group of muscles 200 and a specific muscle 202 from GUI 220. The examiner may then start recording the audio output 140 from the selected muscle 202. When audio output 140 is generated during the EMG testing, EMG processing application 154 processes the audio output 140. The GUI 220 may display a sampling result 206, e.g. if sufficient data is collected for the selected muscle. The device 150 may be configured to not allow an Examiner to select a second muscle for testing unless adequate motor unit sampling has been completed for the first muscle and/or sufficient number of needle passes has been detected.

the electrical activity or only the sound recording can be selected and reviewed separately. In another embodiment the recording can be continuous (in default settings without the need to select individual muscles). The recording can be displayed continuously with recognized events synchronized with the sound recording. Alternatively, a list of time based events or only the sound recording can be reviewed separately. In either case a case the entire recording can be scrolled back and forth. At the end of the EMG testing, the entire file can be saved by the device 150. The data can be saved and exported to the appropriate report generator program.

Figure 3:
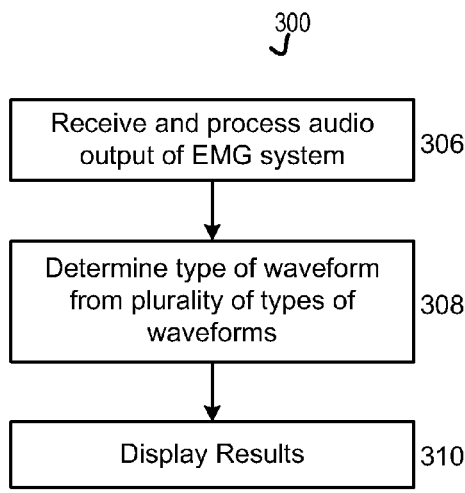
FIG. 3 illustrates a logical flow diagram of an embodiment of a method for analyzing EMG testing results.

FIG. 3 illustrates a logical flow diagram of an embodiment of a method 300 for analyzing EMG testing results. The method 300 begins when the device 150 receives and processes audio output 140 from EMG system 110 in step 306. In step 308, the EMG processing application 154 operating with processing module 152 of device 150 processes the audio output 140 to determine one or more types of waveform from a plurality of types of waveforms in the audio output 140. For example, the device 150 determines that an audio output 140 of an event, such as fibrillation potential, is a type of MUP waveform named "fibrillation potential". In step 310, device 150 then displays the result, e.g. "Fibrillation potential" on the display 156. The time of occurrence of the event and the number of occurrences can be determined and displayed as well.

In another example, the EMG processing application 154 operating with processing module 152 of device 150 determines that audio output 140 is a positive sharp wave and determines that the type of waveform is named "positive sharp wave" and displays this or an abbreviation "PSW" on the display 156. A list of type of waveforms (also called events) that may be determined to be included in the audio output 140 includes, inter alia, Long duration MUP, Short duration MUP, Polyphasic unit, short duration, Polyphasic units long duration, Normal insertion, Increased insertion, Cramp discharge, End-plate noise, End-plate spike, End-plate spike and noise, Fasciculation, Fibrillations, Positive wave, Classic CRD, Stable CRD, Unstable CRD, Slow CRD, Distant CRD, Classic myotonic discharges, Short bursts myotonic discharges, Single myotonic discharge, Distant myotonic discharge, Classic myokymic discharges, Continuous firing myokymic discharges, Single myokymic discharges, Multiple myokymic discharges, Classic neuromyotonic charges, Brief neuromyotonic discharges, Distant neuromyotonic discharge and Tremor Hz.

In addition, the EMG processing application 154 operating with processing module 152 of device 150 is operable to quantify the number of sources of waveforms or events in the audio output 140. The results may be used to populate one or more tables, such as Table 1 above, with waveform data for display and storage. Furthermore, the device 150 may export the results to an appropriate report generator program.

Figure 4:
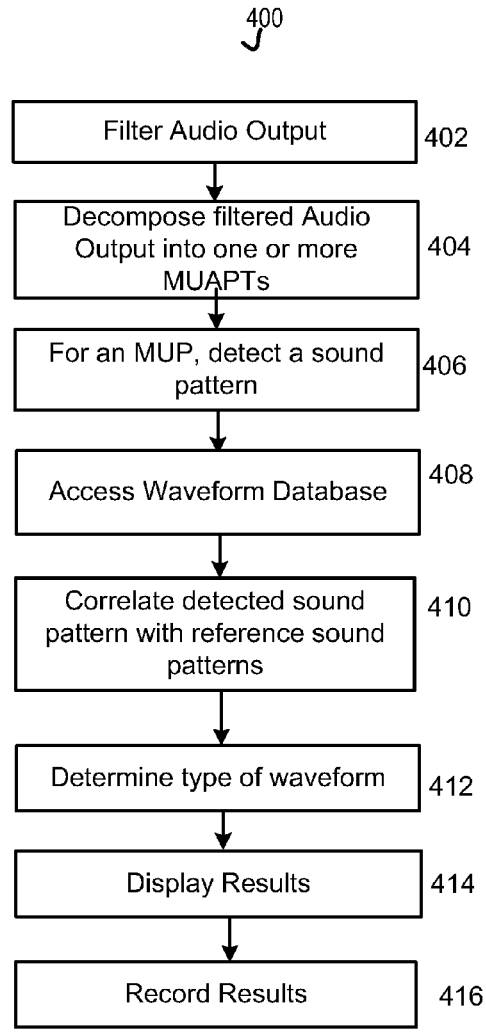
FIG. 4 illustrates a logical flow diagram of an embodiment of another method for analyzing EMG testing results.

FIG. 4 illustrates a logical flow diagram of another embodiment of a method 400 for analyzing EMG testing results. The method 400 includes processing audio output 140 in step 402 to filter the desired electrical activity input events (the desired EMG sound pattern events) from non-desired events, such as speech audio input or noise. In step 404 the filtered audio output is decomposed into one or more source MUAPTs. For example, the filtered audio output 140 may include a plurality of individual motor unit action potential trains (MUAPTs). These individual MUAPTs are identified and may be displayed. For each of the MUP waveforms in an MUAPT, the device 150 detects a sound pattern in step 406. A waveform database is accessed that lists sound patterns and associated types of waveforms in step 408. The detected sound pattern for the waveform is correlated with reference sound patterns until a match is determined in step 410. The type of waveform is thus determined based on the matching reference sound pattern in step 412. The result is displayed in step 414 and recorded in step 416.

Figure 5:
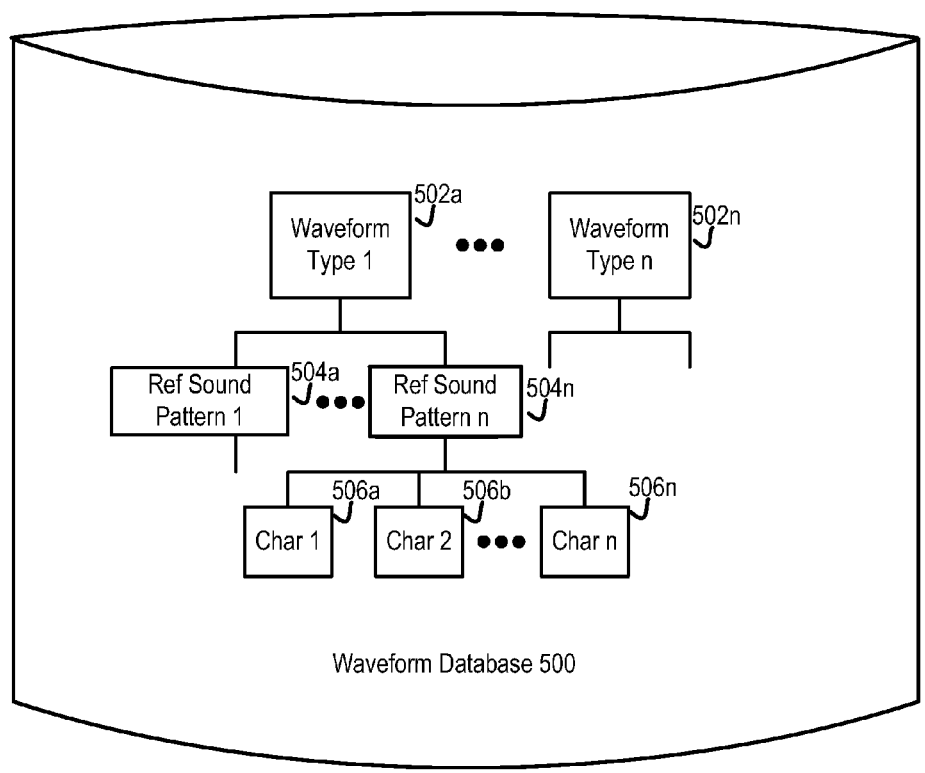
FIG. 5 illustrates a schematic block diagram of an embodiment of a waveform database.

FIG. 5 illustrates a schematic block diagram of an embodiment of a waveform database 500. The waveform database 500 is stored, for example, in device memory 160 or other memory accessible by the EMG processing application 154 or processing module 152 of device 150. The waveform database 500 includes a plurality of waveform types 502 and reference (Ref) sound patterns 504. Since a waveform type 502 may have slight variations, one or more reference sound patterns 504 may be associated with a waveform type 502. Various characteristics (Char) 506 may be stored and associated with a reference sound pattern 504. For example, a characteristic 506 may include a typical duration, peak voltage, number of peaks, repetition rate, etc. for the reference sound pattern. The detected sound pattern for a waveform in a MUAPT is correlated with one or more reference sound patterns in the waveform database 500 until a match is determined. The type of waveform is thus determined based on the matching reference sound patterns from the waveform database 500.

Figure 6:
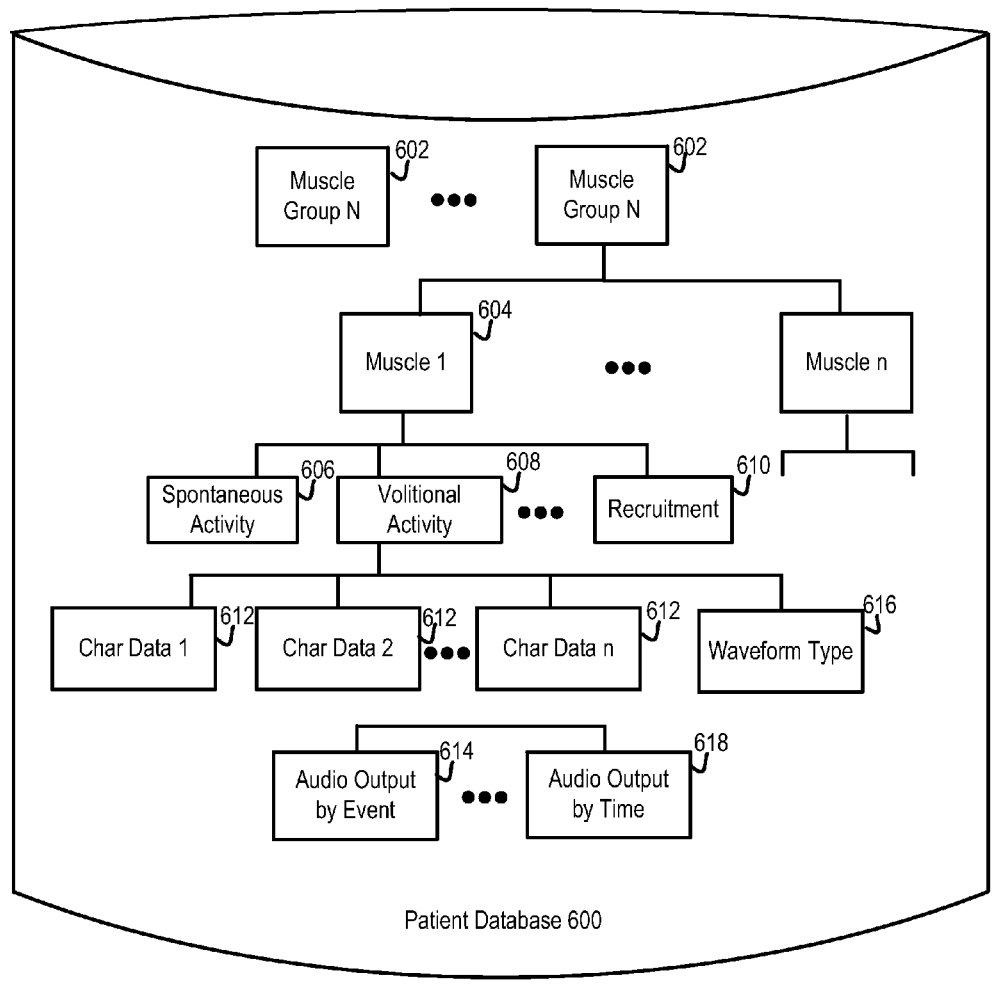
FIG. 6 illustrates a schematic block diagram of an embodiment of a patient database.

FIG. 6 illustrates a schematic block diagram of an embodiment of a patient database 600. The patient database 600 includes EMG testing results for a plurality of patients. For a particular patient, the patient database 600 includes a list of tested muscle groups 602 and one or more tested muscles 604 in each tested muscle group 602. For a tested muscle, the type of condition 608 of the EMG testing is stored, such as spontaneous activity, volitional activity and recruitment. For each type of condition, the one or more detected waveform types 616 are stored as well as characteristic data 612, such as MUP amplitude and duration and other characteristics as shown in Table 1. The audio output 614 is also stored so that it may be retrieved in whole or in part, e.g. audio output by event 614 or audio output by time 618.

For example, the EMG processing application 154 provides a graphical user interface to retrieve the audio output 140 and/or video output 142 for EMG testing of a patient. Time based events may also be replayed, such as recognized sound patterns or waveform types. For example, the sound of a fibrillation potential during testing of a muscle may be retrieved. The time of occurrence of the event is stored and may be retrieved during the audio output 140. The number of occurrences can be determined and stored as one of the characteristics 612. In another embodiment, a duration of the audio output 140, such as between a time 1 and a time 2 may be retrieved of the EMG testing. As such, recording can be displayed continuously with recognized time based events synchronized with the sound recording in step 217. Alternatively, a list of time based events or only the sound recording can be reviewed separately. In another embodiment the recording can be continuous (in default settings without the need to pick individual muscles) again, recording can be displayed continuously with recognized events synchronized with the sound recording. Alternatively, a list of time based events or only the sound recording can be reviewed separately. In either case, the entire recording of the audio output 140 may be scrolled back and forth. At the end of the exam, the entire file can be saved within the device memory 160.

Figures 7, 8:
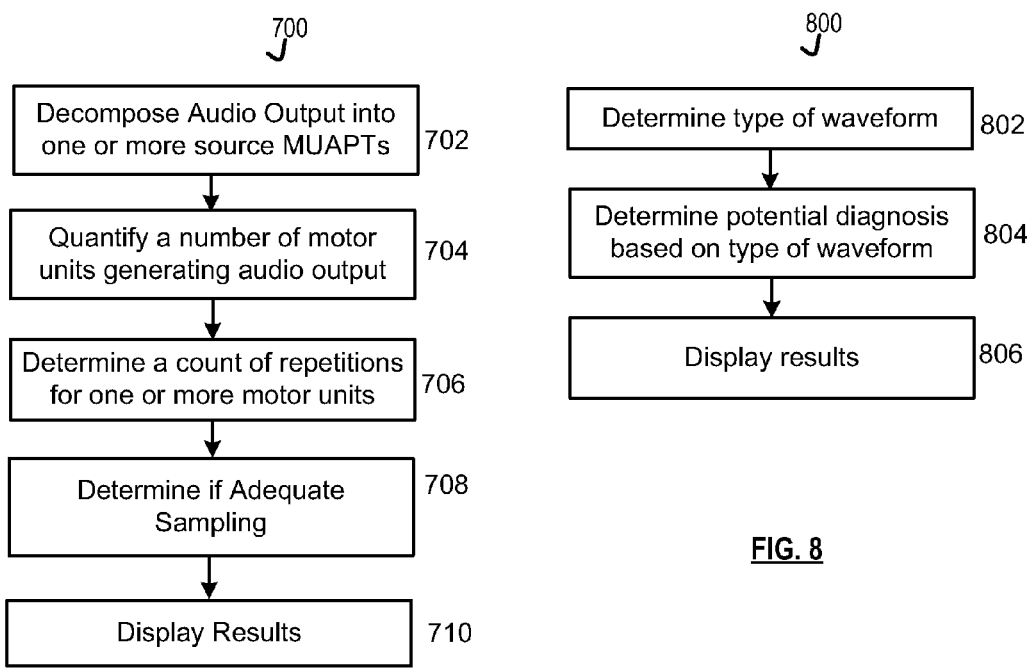
FIG. 7 illustrates a schematic block diagram of an embodiment of another method for analyzing EMG testing results.
FIG. 8 illustrates a schematic block diagram of an embodiment of another method for analyzing EMG testing results.

FIG. 7 illustrates a schematic block diagram of an embodiment of another method 700 for analyzing EMG testing results. In step 702 the filtered audio output is decomposed into one or more source MUAPTs. For example, the filtered audio output 140 may include a plurality of individual motor unit action potential trains (MUAPTs). These individual MUAPTs are identified and may be displayed. MUPs from different motor units tend to have different characteristic shapes, while MUPs recorded by the same electrode from the same motor unit are typically similar. The number of motor units generating the audio output is quantified in step 704. In step 706, a count of repetitions for one or more motor units is determined. In step 708, it is determined if adequate sampling has occurred based on the count of repetitions for the one or more motor units. The results are then displayed in step 710.

FIG. 8 illustrates a schematic block diagram of an embodiment of another method 800 for analyzing EMG testing results. In step 802, type of waveform is determined as described herein. Based on the type of waveform, a potential diagnosis is determined by the EMG processing application 154 and displayed on display 156. For example, abnormal waveforms may be caused by a medical condition, such as neuropathy, nerve dysfunction, plexopathy, carpal tunnel syndrome, myopathy, etc. Based on the determined waveforms, the EMG processing application 154 may display a suggested diagnosis on display 156.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "operably coupled to", "coupled to", and/or "coupling" includes direct coupling between items and/or indirect coupling between items via an intervening item (e.g., an item includes, but is not limited to, a component, an element, a circuit, and/or a module). As may further be used herein, inferred coupling (i.e., where one element is coupled to another element by inference) includes direct and indirect coupling between two items in the same manner as "coupled to". As may even further be used herein, the term "operable to" or "operably coupled to" indicates that an item includes one or more of functions, components, power connections, input(s), output(s), etc., to perform, when activated, one or more its corresponding functions and may further include direct or inferred coupling to one or more other items. As may still further be used herein, the term "associated with", includes direct and/or indirect association or origination or coupling of separate items and/or one item being embedded within another item.

The term "module" is used in the description of the various embodiments of the disclosure. A "module" indicates a device that includes one or more hardware components, such as a single processing device or a plurality of processing devices. A module may also include software stored on memory for performing one or more functions as may be described herein. Note that, the hardware components of a module may operate independently and/or in conjunction with software and/or firmware. As used herein, a module may contain one or more sub-modules, each of which may be one or more modules. As may also be used herein, a module may include one or more additional components.

The description and figures includes functional building blocks. The boundaries and sequence of these functional building blocks may have been arbitrarily defined herein for convenience of description. Alternate boundaries and sequences can be defined so long as the specified functions and relationships are appropriately performed. Any such alternate boundaries or sequences are thus within the scope and spirit of the claimed invention. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The disclosure may have also been described, at least in part, in terms of one or more embodiments. An embodiment of the disclosure is used herein to illustrate the disclosure, an aspect thereof, a feature thereof, a concept thereof, and/or an example thereof. A physical embodiment of an apparatus, an article of manufacture, a machine, and/or of a process that embodies the disclosure may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While particular combinations of various functions and features of the disclosure have been expressly described herein, other combinations of these features and functions are likewise possible. The disclosure is not limited by the particular examples disclosed herein and expressly incorporates these other combinations.

What is claimed is:

1. A device, comprising:
    a display;
    a memory;
    an interface configured to receive audio output of a needle EMG device, wherein a needle electrode is inserted into at least one muscle and records electrical activity of at least one muscle fiber in the at least one muscle and wherein the audio output represents one or more waveforms of the electrical activity of the at least one muscle fiber in the at least one muscle;
    at least one processing device; and
    an electromyography (EMG) processing application stored in the memory and operable with the processing device to:
        process the audio output;
        compare the processed audio output to a plurality of sound patterns;
        detect at least one sound pattern of the plurality of sound patterns using the processed audio output;
        access a waveform database that includes the plurality of sound patterns and associated waveform types of electrical activity of muscle fibers, wherein the associated waveform types of the electrical activity of the muscle fibers include one or more of: insertional activity waveform, spontaneous activity waveform, volitional activity waveform or recruitment waveform;
        determine the identity of the at least one type of waveform of the plurality of types of waveforms from the audio output; and
        display the detected at least one type of waveform on the display.

2. The device of claim 1, wherein the at least one processing device is further operable to:
    diagnose at least one condition based on the detected at least one type of waveform.

3. The device of claim 1, wherein the memory includes the waveform database storing the plurality of reference sound patterns and the associated waveform types of electrical activity of muscle fibers, wherein the associated waveform types of the electrical activity of the muscle fibers include one or more of: Polyphasic units, Normal insertion, Increased insertion, End-plate noise, End-plate spike, Fasciculation, Fibrillations, Positive waves, Complex Repetitive Discharge (CRD) Myotonic discharges, Myokymic discharges, Neuromyotonic discharges.

4. The device of claim 3, wherein the processing device is operable to process the audio output to detect at least one type of waveform of a plurality of types of waveforms from the audio output by:
    detect the sound pattern in the audio output;
    access the waveform database;
    correlate the detected sound pattern with at least one of the plurality of associated waveform types of electrical activity of muscle fibers stored in the waveform database.

5. The device of claim 3, wherein the memory further includes a patient database for storing the audio output and the detected at least one type of waveform.

6. The device of claim 1, wherein the processing device is further operable to:
   quantify a number of motor units generating the audio output; and
   determine a count of repetitions for one or more of the motor units during a portion of the audio output.

7. A method, comprising:
   receiving an audio output of a needle EMG device, wherein the audio output represents electrical activity of at least one muscle fiber;
   processing the audio output;
   identifying a first waveform type in the audio output of the electrical activity of the at least one muscle fiber;
   identifying a second waveform type in the audio output of the electrical activity of the at least one muscle fiber; and
   displaying a first name of the first waveform type and a second name of the second waveform type and a number of each of the first waveform type and the second waveform type on a display, wherein the first waveform type and the second waveform type of the electrical activity of the at least one muscle fiber include two or more of: insertional waveform, spontaneous activity waveform, volitional activity waveform or recruitment waveform.

8. The method of claim 7, further comprising:
   diagnosing at least one condition based on at least one of the first waveform type or the second waveform type.

9. The method of claim 8, further comprising:
   storing a plurality of reference sound patterns and associated waveform types in a waveform database.

10. The method of claim 9, wherein identifying the first waveform type in the audio output of the electrical activity of the at least one muscle fiber in the audio output comprises:
    detecting a sound pattern in the audio output;
    accessing the waveform database;
    correlating the detected sound pattern with one of the plurality of reference sound patterns stored in the waveform database; and
    identifying the associated waveform type in the waveform database with the correlated reference sound pattern.

11. The method of claim 10, further comprising:
    quantifying a number of motor units generating the audio output; and
    determining a count of repetitions for one or more of the motor units during a portion of the audio output.

12. The method of claim 11, further comprising:
    storing a patient database, wherein the patient database includes the audio output and the name of the first waveform type and the second waveform type and the number of the each of the type of the waveforms.

* * * * *